(12) United States Patent
Suzuka et al.

(10) Patent No.: US 11,406,000 B2
(45) Date of Patent: Aug. 2, 2022

(54) ENVIRONMENTAL CONTROL SYSTEM AND ENVIRONMENTAL CONTROL METHOD

(71) Applicant: PANASONIC INTELLECTUAL PROPERTY MANAGEMENT CO., LTD., Osaka (JP)

(72) Inventors: Yuko Suzuka, Kyoto (JP); Saki Aoki, Osaka (JP); Takanori Koshimizu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/312,302

(22) PCT Filed: Dec. 9, 2019

(86) PCT No.: PCT/JP2019/048006
§ 371 (c)(1),
(2) Date: Jun. 9, 2021

(87) PCT Pub. No.: WO2020/121995
PCT Pub. Date: Jun. 18, 2020

(65) Prior Publication Data
US 2022/0030690 A1    Jan. 27, 2022

(30) Foreign Application Priority Data

Dec. 12, 2018   (JP) .............................. JP2018-232424

(51) Int. Cl.
*H05B 47/16*      (2020.01)
*H05B 47/105*    (2020.01)
(Continued)

(52) U.S. Cl.
CPC ............. *H05B 47/16* (2020.01); *A61M 21/02* (2013.01); *H05B 47/105* (2020.01); *A61M 2021/0044* (2013.01)

(58) Field of Classification Search
CPC ........ H05B 45/20; H05B 47/19; H05B 45/10; H05B 47/16; H05B 45/375;
(Continued)

(56) References Cited

U.S. PATENT DOCUMENTS

2013/0063550 A1\* 3/2013 Ritchey .................. G09G 5/026
345/207
2014/0055041 A1\* 2/2014 Ramer ................. H05B 47/175
315/153

FOREIGN PATENT DOCUMENTS

CN        108591973 A      9/2018
JP        2001-041531 A    2/2001
(Continued)

OTHER PUBLICATIONS

Extended European Search Report dated Jan. 14, 2022 issued in the corresponding European Patent Application No. 19894782.2.
(Continued)

*Primary Examiner* — Monica C King
(74) *Attorney, Agent, or Firm* — McDermott Will & Emery LLP

(57) ABSTRACT

An environmental control method, including: receiving settings of a favorite emission color of light that the subject likes and an unfavorite emission color of light that the subject does not like; and switching between first control and second control at a predetermined timing, the first control making a function of a sympathetic nervous system of the subject dominant over a function of a parasympathetic nervous system of the subject by causing an indirect lighting apparatus disposed in a space in which a subject is located and capable of changing an emission color of light to emit
(Continued)

light having the unfavorite emission color of the subject received, the second control making the function of the sympathetic nervous system of the subject dominant over the function of the parasympathetic nervous system of the subject by casing the indirect lighting apparatus to emit light having the favorite emission color of the subject received.

10 Claims, 12 Drawing Sheets

(51) Int. Cl.
*A61M 21/02* (2006.01)
*A61M 21/00* (2006.01)

(58) Field of Classification Search
CPC .... H05B 45/3725; H05B 45/38; H05B 45/24; H05B 47/11; H05B 45/385; H05B 47/10; H05B 47/105; H05B 45/12; H05B 45/48; H05B 45/46; H05B 47/115; H05B 45/14; H05B 45/22; H05B 47/185; H05B 47/195; H05B 33/10; H05B 45/44; H05B 45/30; H05B 45/31; H05B 45/355; H05B 45/37; H05B 45/382; H05B 45/395; H05B 45/40; H05B 47/165; H05B 33/02; H05B 33/14; H05B 44/00; H05B 45/00; H05B 45/18; H05B 45/325; H05B 45/345; H05B 45/39; H05B 45/60; H05B 47/14; H05B 47/17; H05B 47/175; H05B 47/25; H05B 2213/04; H05B 2213/007; H05B 31/50; H05B 33/12; H05B 33/24; H05B 33/26; H05B 33/28; H05B 41/32; H05B 41/34; H05B 45/327; H05B 45/34; H05B 45/397; H05B 45/50; H05B 45/54; H05B 45/56; H05B 45/58; H05B 47/125; H05B 47/13; H05B 47/155; H05B 47/18; H05B 47/23; H05B 47/24; H05B 6/062; H05B 6/1209; H05B 6/6435; G02B 27/0101; G02B 6/0038; G02B 26/101; G02B 2027/014; G02B 27/0955; G02B 6/0036; G02B 6/0051; G02B 27/141; G02B 6/0068; G02B 2027/0118; G02B 26/08; G02B 27/01; G02B 6/0031; G02B 6/005; G02B 6/0055; G02B 2027/0154; G02B 21/367; G02B 23/2453; G02B 26/008; G02B 27/0172; G02B 27/1013; G02B 27/143; G02B 27/30; G02B 27/48; G02B 30/27; G02B 6/0003; G02B 6/0016; G02B 6/0053; G02B 6/1225; G02B 19/0028; G02B 19/0052; G02B 2027/0112; G02B 21/18; G02B 23/04; G02B 26/06; G02B 26/0816; G02B 26/0833; G02B 26/0875; G02B 27/0149; G02B 27/145; G02B 27/146; G02B 27/286; G02B 3/08; G02B 5/02; G02B 5/0278; G02B 5/1809; G02B 5/1842; G02B 5/20; G02B 5/208; G02B 5/28; G02B 6/00; G02B 6/0061; G02B 6/122; G02B 17/004; G02B 19/0014; G02B 19/0076; G02B 2006/12104; G02B 2027/011; G02B 2027/0123; G02B 2027/013; G02B 2027/0178; G02B 2027/0183; G02B 21/361; G02B 26/0808; G02B 26/105; G02B 27/0103; G02B 27/017; G02B 27/0972; G02B 27/0994; G02B 27/1006; G02B 27/126; G02B 27/283; G02B 3/0037; G02B 3/0043; G02B 3/0068; G02B 30/24; G02B 30/25; G02B 30/33; G02B 30/40; G02B 30/50; G02B 5/0215; G02B 5/0221; G02B 5/08; G02B 5/18; G02B 5/1866; G02B 5/201; G02B 5/3025; G02B 6/0006; G02B 6/003; G02B 6/006; G02B 6/0078; G02B 6/124; G02B 6/4214; G02B 6/43; G02B 1/005; G02B 13/0015; G02B 13/18; G02B 17/023; G02B 17/0856; G02B 19/009; G02B 19/0057; G02B 19/0066; G02B 2006/0098; G02B 2006/12121; G02B 2027/0114; G02B 2027/0127; G02B 2027/0138; G02B 2027/0141; G02B 2027/0145; G02B 2027/015; G02B 2027/0159; G02B 2027/0163; G02B 2027/0165; G02B 2027/0174; G02B 2027/0196; G02B 21/0004; G02B 21/0008; G02B 21/0024; G02B 21/0032; G02B 21/0052; G02B 21/0056; G02B 21/006; G02B 21/008; G02B 21/06; G02B 21/086; G02B 21/088; G02B 21/14; G02B 21/368; G02B 23/2469; G02B 23/2476; G02B 26/0841; G02B 26/085; G02B 26/10; G02B 26/12; G02B 26/121; G02B 26/123; G02B 27/0031; G02B 27/0093; G02B 27/0176; G02B 27/0179; G02B 27/0916; G02B 27/0922; G02B 27/1026; G02B 27/104; G02B 27/1073; G02B 27/108; G02B 27/1086; G02B 27/14; G02B 27/142; G02B 27/144; G02B 27/18; G02B 27/28; G02B 3/00; G02B 3/0006; G02B 3/005; G02B 3/0056; G02B 3/02; G02B 3/04; G02B 3/06; G02B 30/28; G02B 30/30; G02B 30/34; G02B 30/35; G02B 30/54; G02B 30/60; G02B 5/005; G02B 5/0242; G02B 5/0252; G02B 5/0284; G02B 5/0294; G02B 5/04; G02B 5/045; G02B 5/0858; G02B 5/09; G02B 5/10; G02B 5/122; G02B 5/132; G02B 5/1819; G02B 5/1823; G02B 5/1861; G02B 5/1885; G02B 5/26; G02B 5/282; G02B 5/30; G02B 5/3083; G02B 5/32; G02B 6/0005; G02B 6/0008; G02B 6/002; G02B 6/0025; G02B 6/0028; G02B 6/0035; G02B 6/0045; G02B 6/0046; G02B 6/0056; G02B 6/0058; G02B 6/0073; G02B 6/0076; G02B 6/0083; G02B 6/0085; G02B 6/009; G02B 6/0095; G02B 6/12; G02B 6/12004; G02B 6/1226; G02B 6/29323; G02B 6/30; G02B 6/34; G02B 6/3636; G02B 6/423; G02B 6/4249; G02B 6/4298; G02B 6/50; G02B 7/006; G02B 7/08; G02B 7/09; G02B 7/36; G02B 7/40; G02F 1/29; G02F 1/133603; G02F 1/295; G02F 1/13306; G02F 1/133606; G02F 1/291; G02F 1/292; G02F 1/2955; G02F 1/133; G02F 1/133605; G02F 1/133608; G02F 1/133611; G02F 1/134309; G02F 1/1347; G02F 1/137; G02F 2201/302; G02F 1/0105; G02F 1/0136; G02F 1/035; G02F 1/13; G02F 1/1323; G02F 1/1326; G02F 1/13312; G02F 1/13318; G02F 1/1333;

G02F 1/133302; G02F 1/133371; G02F 1/1334; G02F 1/13345; G02F 1/133504; G02F 1/133526; G02F 1/1336; G02F 1/133601; G02F 1/133627; G02F 1/1339; G02F 1/13398; G02F 1/134381; G02F 1/13476; G02F 1/2252; G02F 1/2257; G02F 1/294; G02F 1/3511; G02F 1/353; G02F 2201/063; G02F 2201/30; G02F 2201/34; G02F 2201/38; G02F 2202/04; G02F 2202/10; G02F 2202/20; G02F 2202/28; G02F 2202/42; G02F 2203/07; G02F 2203/48; G02F 2203/62; H05K 13/0812; H05K 2201/10106; H05K 1/0203; H05K 1/0256; H05K 1/0271; H05K 1/0296; H05K 1/0393; H05K 1/056; H05K 1/147; H05K 1/148; H05K 1/181; H05K 1/189; H05K 13/0413; H05K 2201/0129; H05K 2201/0145; H05K 2201/0154; H05K 2201/0195; H05K 2201/055; H05K 2201/10121; H05K 3/202; H05K 3/284; H05K 3/301; H05K 5/0247; H05K 5/06; H05K 7/00

See application file for complete search history.

(56) References Cited

FOREIGN PATENT DOCUMENTS

| | | |
|---|---|---|
| JP | 2017-116236 A | 6/2017 |
| WO | 2014/111821 A1 | 7/2014 |

OTHER PUBLICATIONS

Office Action dated Feb. 18, 2022 issued in the corresponding Indian Patent Application No. 202117023129, with English translation.

International Search Report and Written Opinion issued in International Patent Application No. PCT/JP2019/048006, dated Feb. 18, 2020; with partial English translation.

* cited by examiner

FIG. 12

| Biological information | Parasympathetic nervous system is increasingly functioning | Sympathetic nervous system is increasingly functioning |
|---|---|---|
| Body temperature | High ⇕ | Low |
| Blood pressure | Decreasing ⇕ | Increasing |
| Heart rate | Decreasing ⇕ | Increasing |
| Pulse wave | Slow ⇕ | Fast |
| Amount of sweating | Decreasing ⇕ | Increasing |
| Pupil diameter | Shrinking ⇕ | Enlarging |
| Epidermis temperature | High ⇕ | Low |
| Facial expression | Calm ⇕ | Lively |

ENVIRONMENTAL CONTROL SYSTEM AND ENVIRONMENTAL CONTROL METHOD

CROSS-REFERENCE OF RELATED APPLICATIONS

This application is the U.S. National Phase under 35 U.S.C. § 371 of International Patent Application No. PCT/JP2019/048006, filed on Dec. 9, 2019, which in turn claims the benefit of Japanese Application No. 2018-232424, filed on Dec. 12, 2018, the entire disclosures of which Applications are incorporated by reference herein.

TECHNICAL HELD

The present invention relates to an environmental control system and an environmental control method.

BACKGROUND ART

Patent Literature 1 discloses an environmental control apparatus which detects physical states of a resident by using both biological information and behavior information, and controls housing equipment most appropriately for the individual based on the physical states.

CITATION LIST

Patent Literature

[PTL 1] Japanese Unexamined Patent Application Publication No. 2001-041531

SUMMARY OF INVENTION

Technical Problem

The human autonomic nervous system consists of two kinds of nervous systems that are a sympathetic nervous system and a parasympathetic nervous system which function in contrast. The functions of the organs of a human are maintained by these two kinds of nervous systems functioning in good balance. In modern times, an increased number of people complain about health problems that occur due to imbalance in the autonomic nervous system caused by irregular lifestyles, habits, and so on.

The present invention provides the environmental control system and the environmental control method which make it possible to reduce the disorder of the autonomic nervous system of a subject.

Solution to Problem

An environmental control system according to an aspect of the present invention includes: an indirect lighting apparatus which is disposed in a space in which a subject is located and is capable of changing an emission color of light; a setting apparatus which receives settings of a favorite emission color of light that the subject likes and an unfavorite emission color of light that the subject does not like; and a control apparatus which switches between first control and second control at a predetermined timing, the first control making a function of a sympathetic nervous system of the subject dominant over a function of a parasympathetic nervous system of the subject by causing the indirect lighting apparatus to emit light having the unfavorite emission color of the subject received by the setting apparatus, the second control making the function of the sympathetic nervous system of the subject dominant over the function of the parasympathetic nervous system of the subject by casing the indirect lighting apparatus to emit light having the favorite emission color of the subject received by the setting apparatus.

An environmental control method according to an aspect of the present invention includes: receiving settings of a favorite emission color of light that the subject likes and an unfavorite emission color of light that the subject does not like; and switching between first control and second control at a predetermined timing, the first control making a function of a sympathetic nervous system of the subject dominant over a function of a parasympathetic nervous system of the subject by causing an indirect lighting apparatus which is disposed in a space in which a subject is located and is capable of changing an emission color of light to emit light having the unfavorite emission color of the subject received, the second control making the function of the sympathetic nervous system of the subject dominant over the function of the parasympathetic nervous system of the subject by casing the indirect lighting apparatus to emit light having the favorite emission color of the subject received.

Advantageous Effects of Invention

According to the present invention, it is possible to implement the environmental control system and the environmental control method which make it possible to reduce the disorder of the autonomic nervous system of the subject.

BRIEF DESCRIPTION OF DRAWINGS

FIG. 12 is a diagram illustrating a relationship between the function of the sympathetic nervous system and the function of the parasympathetic nervous system, and change in biological information.

DESCRIPTION OF EMBODIMENTS

Hereinafter, embodiments according to the present disclosure are described with reference to the drawings. It is to be noted that each of the embodiments described below indicates a general or specific example. The numerical values, shapes, materials, constituent elements, the arrangement and connection of the constituent elements, etc. indicated in the following embodiments are mere examples, and do not limit the scope of the present invention. Among the constituent elements in the following embodiments, constituent elements not recited in the independent claim that defines the most generic concept of the present disclosure are described as optional constituent elements.

It is to be noted that each of the drawings is a schematic diagram, and is not necessarily illustrated precisely. In addition, in each of the drawings, substantially the same constituent elements may be assigned with the same numerical signs, and overlapping descriptions may be omitted or simplified.

Embodiment

[A Configuration of an Environmental Control System]

Figure 1:
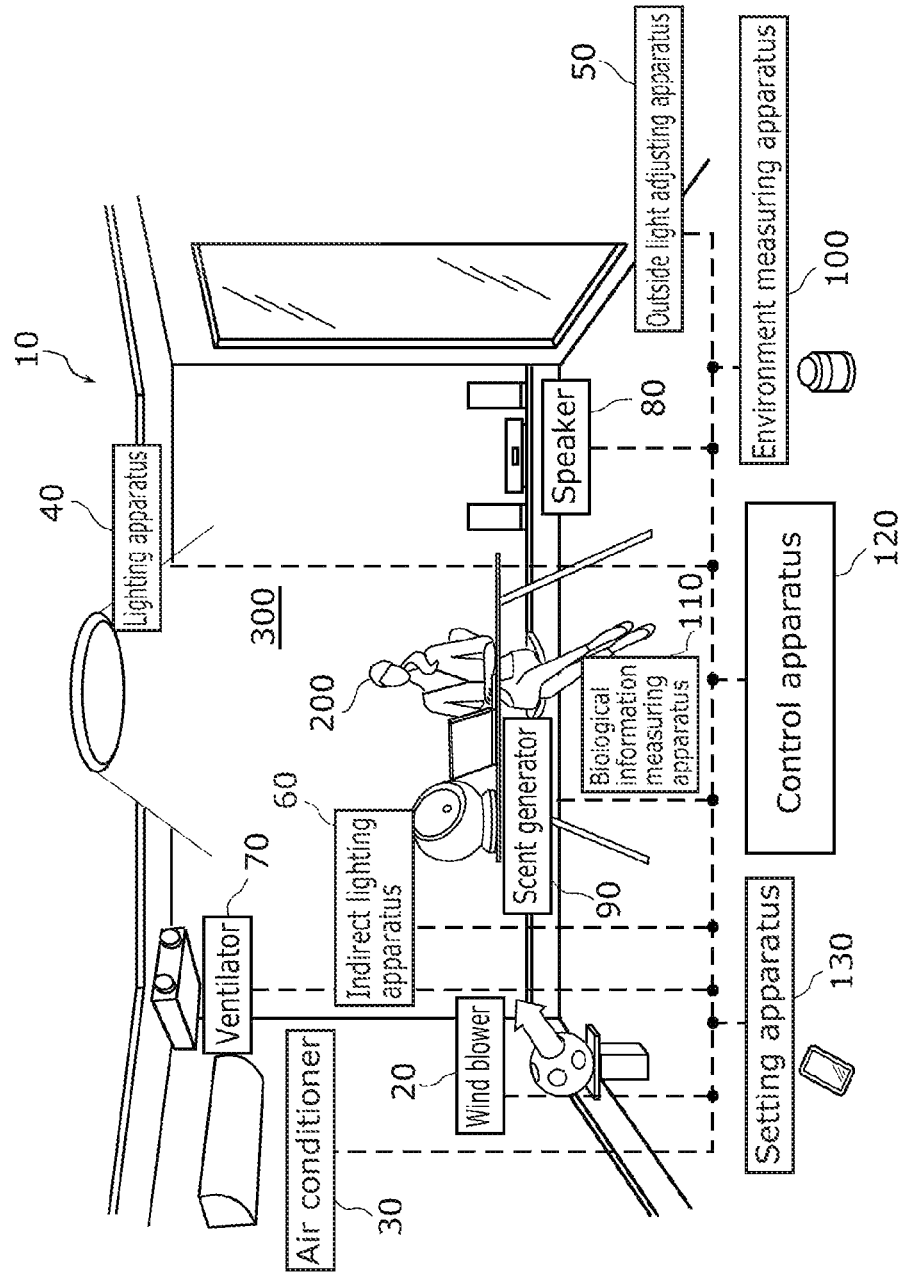
FIG. 1 is a diagram illustrating a configuration of an environmental control system according to an embodiment.

First, a configuration of the environmental control system according to an embodiment is described. FIG. 1 is a diagram illustrating a configuration of the environmental control system according to the embodiment.

Environmental control system 10 illustrated in FIG. 1 performs control for adjusting the function of the autonomic nervous system of subject 200 by controlling target apparatuses related to an environment in space 300 which is a closed space such as a room.

The autonomic nervous system of a human consists of two kinds of nervous systems that are the sympathetic nervous system and the parasympathetic nervous system which function in contrast. The functions of the organs of the human are maintained by these two kinds of nervous systems functioning in good balance. Environmental control system 10 switches between first control and second control at a predetermined timing, First control makes a function of a sympathetic nervous system of a subject dominant over a function of a parasympathetic nervous system of the subject, and second control makes the function of the parasympathetic nervous system of the subject dominant over the function of the sympathetic nervous system of the subject. In this way, it is possible to reduce the disorder of the autonomic nervous system of subject 200.

Specifically, environmental control system 10 includes wind blower 20, air conditioner 30, lighting apparatus 40, outside light adjusting apparatus 50, indirect lighting apparatus 60, ventilator 70, speaker 80, scent generator 90, environment measuring apparatus 100, biological information measuring apparatus 110, control apparatus 120, and setting apparatus 130.

Wind blower 20 is an apparatus which blows wind toward subject 200. Specifically, wind blower 20 is a wind blower which has a comparatively high directivity such as a circulator, and may be a fan. Alternatively, for example, a wind blower which is linked with a sensor and has a swing function is capable of obtaining position information of subject 200 via the sensor and thus is capable of blowing wind from the wind blower toward subject 200 based on the position information. The wind blower is capable of blowing a necessary amount of wind toward subject 200 by also performing strength control of the wind amount based on distance information included in the position information. The wind blower is further capable of blowing an appropriate amount of wind toward subject 200 who is moving in a room while tracking subject 200 by always obtaining position information of subject from the sensor.

Air conditioner 30 is an apparatus for adjusting a temperature in space 300 in which subject 200 is located. Air conditioner 30 is capable of adjusting a humidity in space 300. Air conditioner 30 makes the temperature and the humidity in space 300 closer to a temperature and a humidity directed by control apparatus 120.

Lighting apparatus 40 is an apparatus for direct lighting which illuminates space 300 in which subject 200 is located. Lighting apparatus 40 is, for example, a ceiling light including a light emitting element such as an LED as a light source. Lighting apparatus 40 may be another lighting apparatus such as a base light or a down light. Lighting apparatus 40 is capable of being subjected to light adjustment and color adjustment by control apparatus 120.

Outside light adjusting apparatus 50 is an apparatus which adjusts the amount of light that enters space 300 in which subject 200 is located. Outside light adjusting apparatus 50 is, for example, an electronic blind which can be implemented in the form of a light adjusting film. Outside light adjusting apparatus 50 may be electric blinds (electric shutters) or the like.

Indirect lighting apparatus 60 is an apparatus for indirect lighting disposed in space 300 in which subject 200 is located. Indirect lighting apparatus 60 is disposed, for example, in a place at which one or more light sources (or the whole of indirect lighting apparatus 60) is not directly seen, and indirectly illuminates space 300 by causing light to reflect on, for example, a wall, a ceiling, or the like. In other words, indirect lighting apparatus 60 directly illuminates one or more structures such as walls, the ceiling, etc. which define space 300.

For example, indirect lighting apparatus 60 is capable of changing emission colors of light by including a plurality of light sources which provide different emission colors. For example, indirect lighting apparatus 60 includes a light source which emits red light, a light source which emits green light, a light source which emits blue light, and changing emission colors of light by adjusting the luminance of light that is emitted by each light source. Indirect lighting apparatus 60 may provide optional emission colors by combining any of the light sources and optical filters. As indirect lighting apparatus 60, for example, a spot light, a stand light, a bracket light, a pendant light, a line illuminator, or the like is used.

As described later, the Inventors have found out that it is possible to make the function of the sympathetic nervous system of subject 200 dominant over the function of the parasympathetic nervous system of subject 200 by causing indirect lighting apparatus 60 to emit light having an unfavorite emission color of subject 200. The Inventors also have found out that it is possible to make the function of the parasympathetic nervous system of subject 200 dominant over the function of the sympathetic nervous system of subject 200 by causing indirect lighting apparatus 60 to emit light having a favorite emission color of subject 200. Such control using indirect lighting apparatus 60 is described in detail later in the section of [Other Control Using the Indirect Lighting Apparatus].

Ventilator 70 ventilates space 300 in which subject 200 is located. Ventilator 70 does not have a temperature adjusting function, unlike air conditioner 30. Ventilator 70 is, for example, an Energy Recovery Ventilator (ERV). Ventilator 70 may be a ventilator which does not perform heat exchange such as a ventilation fan. Alternatively, ventilator 70 may be an open/close apparatus of a window installed in space 300.

Speaker 80 is an apparatus which is disposed in space 300 in which subject 200 is located, and outputs speech, music, or the like.

Scent generator 90 is an apparatus which is disposed in space 300 in which subject 200 is located, and generates a scent. Scent generator 90 is, for example, an aroma diffuser, and may be a generator which generates another scent.

Environment measuring apparatus 100 is an apparatus which measures environmental information in space 300 in which subject 200 is located. Environment measuring apparatus 100 is, for example, a temperature sensor which measures temperature in space 300, a humidity sensor which measures humidity in space 300, an illuminance sensor which measures illuminance in space 300, a $CO_2$ sensor which measures the concentration of carbon dioxide ($CO_2$) in space 300, or the like.

Biological information measuring apparatus 110 is an apparatus which measures biological information about subject 200. Biological information measuring apparatus 110 measures, as biological information, a body temperature, a blood pressure, a heart rate, a pulse wave, the amount of sweating, an epidermis temperature, a facial expression, etc. of subject 200. Biological information measuring apparatus 110 may measure a Very Low Frequency (VLF), a High Frequency (HF), a Low Frequency (LF), LF/HF, inspiration time, exhaustion time, pause time, etc, which are calculated based on the heart rate, the pulse wave, and a respiratory variation waveform. Biological information measuring apparatus 110 is, for example, a wearable sensor (that is, a contact sensor) which is attached to the body of subject 200, and may be a non-contact sensor. Examples of such a non-contact sensor includes a radio wave sensor capable of measuring heart rates, respiratory rates, pulse waves, etc. and a camera capable of measuring pupil diameters or facial expressions.

Figure 2:
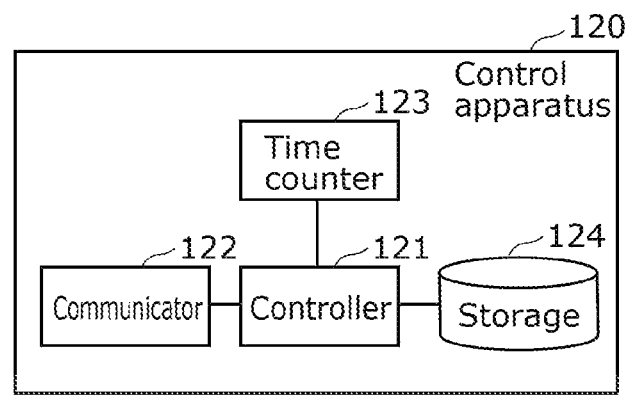
FIG. 2 is a block diagram illustrating a functional configuration of a control apparatus.

Control apparatus 120 is an apparatus which controls target apparatuses such as wind blower 20, air conditioner 30, lighting apparatus 40, outside light adjusting apparatus 50, indirect lighting apparatus 60, ventilator 70, speaker 80, and scent generator 90. FIG. 2 is a block diagram illustrating a functional configuration of control apparatus 120.

As illustrated in FIG. 2, control apparatus 120 includes controller 121, communicator 122, time counter 123, and storage 124.

Controller 121 controls target apparatuses by causing communicator 122 to transmit control signals. Controller 121 may be implemented in the form of, for example, a microcomputer, but may be implemented in the form of a processor.

Communicator 122 is a communication circuit (in other words, a communication module) which allows control apparatus 120 to communicate with the target apparatuses. For example, communicator 122 transmits control signals to target apparatuses under control of controller 121. In addition, communicator 122 receives environmental information about space 300 from environment measuring apparatus 100, and receives biological information of subject 200 from biological information measuring apparatus 110. Communicator 122 may perform wireless communication for example, but may perform wired communication. Communication standards for communication that is performed by communicator 122 are not particularly limited.

Time counter 123 measures current time. Time counter 123 is implemented in the form of a real time clock for example.

Storage 124 is a storage apparatus in which a control program allowing controller 121 to control each target apparatus is stored. Storage 124 is implemented in the form of a semiconductor memory for example.

Setting apparatus 130 is a user interface apparatus which receives, from a user such as subject 200, an operation (for example, a setting operation regarding first control that makes the function of the sympathetic nervous system dominant, or a setting operation regarding second control that makes the function of the parasympathetic nervous system dominant). The details of the setting received by setting apparatus 130 are transmitted to control apparatus 120 as setting information. Setting apparatus 130 is, for example, a mobile terminal such as a smartphone or a tablet terminal, but may be an operation panel disposed on a wall, or the like. It is to be noted that setting apparatus 130 may be implemented as a part of another apparatus. For example, setting apparatus 130 may be implemented as an operation receiver provided in control apparatus 120. An operation receiver is specifically implemented in the form of a touch panel, hardware buttons, or the like.

[First Control: Control on the Wind Blower]

Figure 3:
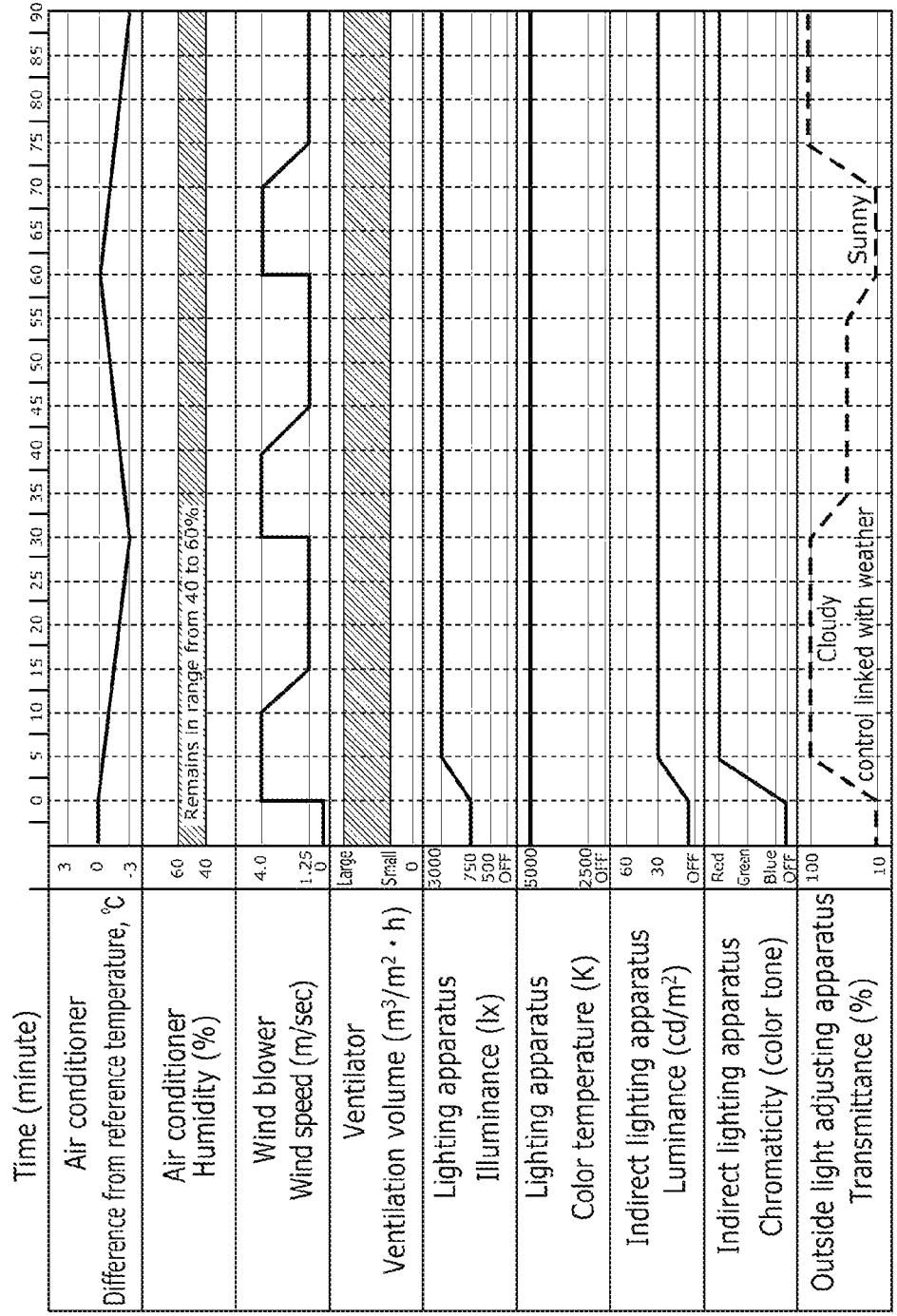
FIG. 3 is a time chart for explaining first control which makes a function of a sympathetic nervous system of a subject dominant.

As described above, environmental control system 10 is capable of performing the first control making the function of the sympathetic nervous system of subject 200 dominant. Hereinafter, details of the first control are described. FIG. 3 is a time chart for explaining the first control making the function of the sympathetic nervous system of subject 200 dominant. It is assumed that, in FIG. 3, the start time of the first control is 0 minute, and as one example, target apparatuses are being controlled with consideration of only comfortableness before the start time. Although a period from 0 minute to 90 minutes is illustrated in FIG. 3, the same control as performed in the period from 0 minute to 90 minutes is repeated after the period.

It is to be noted that, in the first control making the function of the sympathetic nervous system dominant, it is only necessary that at least one of the target apparatuses be controlled, but two or more of the target apparatuses may be controlled. In this way, stimuli given to subject 200 are increased, and thus it is possible to make the function of the sympathetic nervous system to further dominant.

First, control on wind blower 20 is described. Wind blower 20 is disposed at a position at which wind blower 20 can blow wind to body parts of subject 200 with exposed skin such as the arms, neck, and face. Wind blower 20 is disposed so that head wind is blown to the face of subject 200, for example. Direct touch of wind on the body surface of subject 200 gives strong stimuli which can cause, for example, decrease in feeling temperature of subject 200 and decrease in oxygen concentration around the face of subject 200. This makes the function of the sympathetic nervous system dominant.

In the installation condition, controller 121 of control apparatus 120 causes wind blower 20 to change the wind speed of wind to be blown at a predetermined cycle in a range from 15 minutes to 60 minutes. In addition, controller 121 sets a time during which a wind speed is a smallest value to less than 50% of the predetermined cycle. Such temporal changes in wind speed constantly give stimuli by wind to subject 200 (prevent subject 200 from getting used to the stimuli by wind) and reduce the degree of fatigue of subject 200. This makes it easier to maintain the state in which the function of the sympathetic nervous system is dominant.

More specifically, controller 121 causes wind blower 20 to change the wind speed of the wind to be blown at a 30-minute cycle. In general, it is considered that human concentration lasts approximately from 15 minutes to 60 minutes. Thus, change in wind speed at the predetermined cycle in the range from 15 minutes to 60 minutes (for example, the 30-minute cycle) gives stimuli to subject 200 effectively. Although the time during which the wind speed is the smallest value corresponds to 50% of the predetermined cycle in the example in FIG. 3, the time may correspond to 50% or less of the predetermined cycle.

The wind speed of the wind to be blown by wind blower 20 reaches a largest value (for example, 4.0 m/sec) immediately after the start of control, and is maintained at the largest value for 10 minutes. Subsequently, the wind speed decreases linearly for 5 minutes to reach the smallest value (for example, 1.25 m/sec), and is maintained at the smallest value for 15 minutes. In other words, the time (for example, close to 0) from when the wind speed of the wind to be blown by wind blower 20 changes from the smallest value to the largest value is shorter than the time (for example, 5 minutes) from when the wind speed of the wind to be blown by wind blower 20 changes from the largest value to the smallest value.

In this way, a time from when the wind speed of the wind to be blown by wind blower 20 becomes a smallest value to when the smallest value changes to a largest value is set to a comparatively short time, which makes it possible to give stimuli to subject 200 effectively. Furthermore, since a time from when the wind speed of the wind to be blown by wind blower 20 becomes a smallest value to when the smallest value changes to a largest value is set to a comparatively short time, it is possible to prevent subject 200 from feeling strange.

Figure 4:
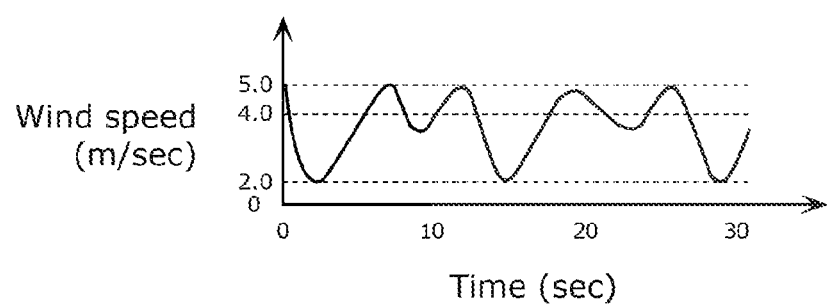
FIG. 4 is a diagram illustrating one example of fluctuation of wind speed.

Although not illustrated precisely in FIG. 3, controller 121 changes the wind speed of the wind blown by wind blower 20 from a largest fluctuation value (for example, 5.0 m/sec) to a smallest fluctuation value (for example, 1.0 m/sec), based on the largest value (for example, 4.0 m/sec). In other words, although the wind speed looks changing linearly in FIG. 3, the wind speed actually changes more finely in the linear change. Hereinafter, such a change in wind speed is also referred to as a "fluctuation". FIG. 4 is a diagram illustrating one example of such a fluctuation in wind speed.

The fluctuation in wind speed is a 1/f fluctuation for example, but may be a random fluctuation. The 1/f fluctuation means a fluctuation in which a power spectrum density is inverse proportional to frequency f. The fluctuation in wind speed is formed at a cycle on the order of several seconds that is in a range approximately from 1 second to 10 seconds. In other words, controller 121 fluctuates the wind speed of the wind to be blown by wind blower 20 at a time interval shorter than the predetermined cycle (30-minute cycle).

Such a constant change in wind speed can give constant stimuli by wind to subject 200 (prevent subject 200 from getting used to the stimuli by wind), which makes it easier to maintain a state in which the function of the sympathetic nervous system is dominant. In addition, a non-cyclical fluctuation can give constant stronger stimuli by wind to subject 200 (prevent subject 200 from getting used to the stimuli by wind).

[First Control: Control on the Other Target Apparatuses]

Hereinafter, control on the other target apparatuses is described while further referring to FIG. 3.

First, control on air conditioner 30 is described. Controller 121 increases and decreases a surrounding temperature around subject 200 using air conditioner 30. Controller 121 decreases the surrounding temperature by 3 degrees Celsius for 30 minutes in an initial period from the start of first control making the function of the sympathetic nervous system dominant, and then increases the decreased surrounding temperature by 3 degrees Celsius for 30 minutes. It is desirable that temperatures be changed within 30 minutes. After the above changes, such temperature changes are repeated. Reference temperatures differ depending on seasons. For example, reference temperatures are 26 degrees Celsius in summer, 22 degrees Celsius in spring and autumn, and 20 degrees Celsius in winter. In order to make the function of the sympathetic nervous system dominant, there are cases in which a temperature may be changed by 3 degrees Celsius or more. With consideration of health, it is only necessary that temperatures change within 5 degrees Celsius. In the example of FIG. 3, temperatures change by 3 degrees Celsius.

A surrounding temperature around subject 200 is measured by, for example, environment measuring apparatus 100. Controller 121 controls air conditioner 30 based on the temperature measured by environment measuring apparatus 100. Controller 121 may increase and decrease a temperature to be set of air conditioner 30 at the 60-minute cycle as described above without using environment measuring apparatus 100.

In this way, controller 121 increases and decreases the temperature at predetermined cycles (for example, at the 60-minutes cycles). Such temporal changes in temperature constantly give stimuli by temperatures to subject 200 (prevent subject 200 from getting used to the stimuli by temperatures) and reduce the degree of fatigue of subject 200. This makes it easier to maintain the state in which the function of the sympathetic nervous system of subject 200 is dominant.

Controller 121 adjusts timings at which switching from increase to decrease and switching from decrease to increase in the surrounding temperature around subject 200 are made to timings at which the wind speed of the wind to be blown by wind blower 20 is increased. In other words, the wind speed of the wind to be blown by wind blower 20 is increased when the increase and decrease in the surrounding temperature around subject 200 are switched. In this way, the temperature change is made as another stimulus at the timing at which wind blower 20 increases the wind speed, that is, at the timing at which the stimulus to subject 200 is increased. Thus, stimuli are further increased. Accordingly, it is possible to make the function of the sympathetic nervous system of subject 200 further dominant.

Controller 121 keeps a humidity in space 300 in a range from 40% to 60% using air conditioner 30 during the first control making the function of the sympathetic nervous system dominant.

Next, control on lighting apparatus 40 is described. Controller 121 increases an illuminance in space 300 using lighting apparatus 40 when the wind speed of the wind to be blown by wind blower 20 increases firstly (in other words, in the initial period from the start of the first control making the function of the sympathetic nervous system dominant). Controller 121 increases the illuminance in space 300 up to 300 lx for 5 minutes from the start of the control. It is desirable that the illuminance be changed with time in such a manner that subject 200 does not feel uncomfortable due to illuminance changes.

In this way, increasing the luminous intensity in space 300 can make the function of the sympathetic nervous system of subject 200 dominant.

Furthermore, controller 121 increases the color temperature of light emitted by lighting apparatus 40 when the wind speed of the wind to be blown by wind blower 20 increases firstly. Although the color temperature does not change in the example in FIG. 3, control for increasing a color temperature before the start of control is performed when the color temperature is low. It is desirable that the chromaticity be changed with time in such a manner that subject 200 does not feel uncomfortable due to chromaticity changes.

In this way, providing space 300 with an illuminance environment in which the color temperature is high can make the function of the sympathetic nervous system of subject 200 dominant.

Next, control on outside light adjusting apparatus 50 is described. Controller 121 increases the light amount of outside light that enters space 300 using outside light adjusting apparatus 50 when the wind speed of the wind to be blown by wind blower 20 increases firstly (in other words, in the initial period from the start of the first control making the function of the sympathetic nervous system dominant). Specifically, controller 121 increases a light transmittance of outside light adjusting apparatus 50. It is desirable that the illuminance be changed with time in such a manner that subject 200 does not feel uncomfortable due to illuminance changes.

In this way, increasing the luminous intensity in space 300 can make the function of the sympathetic nervous system of subject 200 dominant.

It is to be noted that controller 121 may then control outside light adjusting apparatus 50 depending on a weather. Weather-based control is performed based on an illuminance indicated by an illuminance sensor included in outside light adjusting apparatus 50. For example, controller 121 sets a light transmittance of outside light adjusting apparatus 50 to 100% when the weather is cloudy (when the illuminance indicated by the illuminance sensor is comparatively low), and decreases a light transmittance to approximately 10% for the purpose of reducing glare, and so on, when the weather is sunny (when the illuminance indicated by the illuminance sensor is comparatively high).

Next, control on indirect lighting apparatus 60 is described. Controller 121 changes the emission color of light to be emitted by indirect lighting apparatus 60 when the wind speed of the wind to be blown by wind blower 20 increases firstly (in other words, in the initial period from the start of the first control making the function of the sympathetic nervous system dominant). For example, controller 121 increases a luminance (substantially, an illuminance) from 0 (colorless) $cd/m^2$ to 30 $cd/m^2$ for 5 minutes from the start of the control. The emission color at this time is red for example, but may be orange, or another color. It is only necessary that controller 121 change the chromaticity of light to be emitted by indirect lighting apparatus 60 in such a manner that the x-coordinate in a chromaticity diagram of a CIE 1931 color space of the chromaticity increases in the initial period from the start of the first control making the function of the sympathetic nervous system dominant. This can make the function of the sympathetic nervous system of subject 200 dominant.

Alternatively, controller 121 may cause indirect lighting apparatus 60 to emit light having an unfavorite emission color of subject 200 in the first control making the function of the sympathetic nervous system dominant. The Inventors have found out that it is possible to make the function of the sympathetic nervous system dominant effectively more than a case in which other apparatuses such as wind blower 20 are controlled, by causing indirect lighting apparatus 60 to emit light having the unfavorite emission color of subject 200. Such control of causing indirect lighting apparatus 60 to emit light having an unfavorite emission color of subject 200 is described in detail later in the section of [Other Control Using the Indirect Lighting Apparatus].

Controller 121 fluctuates the illuminance of the light to be emitted by indirect lighting apparatus 60 although the control is not precisely illustrated in FIG. 3. In other words, the brightness of the light to be emitted by indirect lighting apparatus 60 is increased or decreased at one or more cycles of several seconds that is in a range approximately from 1 second to 10 seconds (a constant cycle or random cycles are possible). The light to be emitted by indirect lighting apparatus 60 may fluctuate with constant amplification or with random amplification. For example, controller 121 may fluctuate the illuminance of the light to be emitted by indirect lighting apparatus 60 as indicated by a wind speed waveform in FIG. 4.

Such constant change in illuminance gives stimuli by indirect light to subject 200 (prevent subject 200 from getting used to the stimuli by indirect light), which makes it easier to keep subject 200 in the state in which the function of the sympathetic nervous system is dominant.

Next, control on ventilator 70 is described. Controller 121 sets the concentration of carbon dioxide in space 300 to 1000 ppm or less using ventilator 70, 1000 ppm is one example of a predetermined concentration. For example, controller 121 sets the concentration of carbon dioxide in space 300 to 1000 ppm or less by increasing the ventilation volume of ventilator 70 when the concentration of the carbon dioxide in space 300 is high. For example, the concentration of the carbon dioxide in space 300 is measured by environment measuring apparatus 100, and controller 121 controls ventilator 70 based on the concentration of the carbon dioxide measured by environment measuring apparatus 100.

In this way, decreasing the concentration of the carbon dioxide in space 300 can make the function of the sympathetic nervous system of subject 200 dominant.

Next, control on speaker 80 and scent generator 90 is described. Controller 121 changes a sound to be output by speaker 80 when the wind speed of the wind to be blown by wind blower 20 increases. "Changing a sound" here includes starting to output a sound in a state in which no sound is output. For example, speaker 80 outputs a comparatively up-tempo musical piece. In this way, the sound change is made as another stimulus at the timing at which wind blower 20 increases the wind speed, that is, at the timing at which the stimulus to subject 200 is increased. Thus, stimuli are further increased. Accordingly, it is possible to make the function of the sympathetic nervous system of subject 200 further dominant.

Controller 121 changes a scent to be generated by scent generator 90 when the wind speed of the wind to be blown by wind blower 20 increases. "Changing a scent" here includes starting to generate a scent in a state in which no scent is generated. For example, scent generator 90 generates a scent with a comfortable stimulus such as a scent of mint. In this way, the scent change is made as another stimulus at the timing at which wind blower 20 increases the wind speed, that is, at a timing at which the stimulus to subject 200 is further increased. Thus, stimuli are further increased. Accordingly, it is possible to make the function of the sympathetic nervous system of subject 200 further dominant.

[Second Control: Control on the Air Conditioner]

Figure 5:
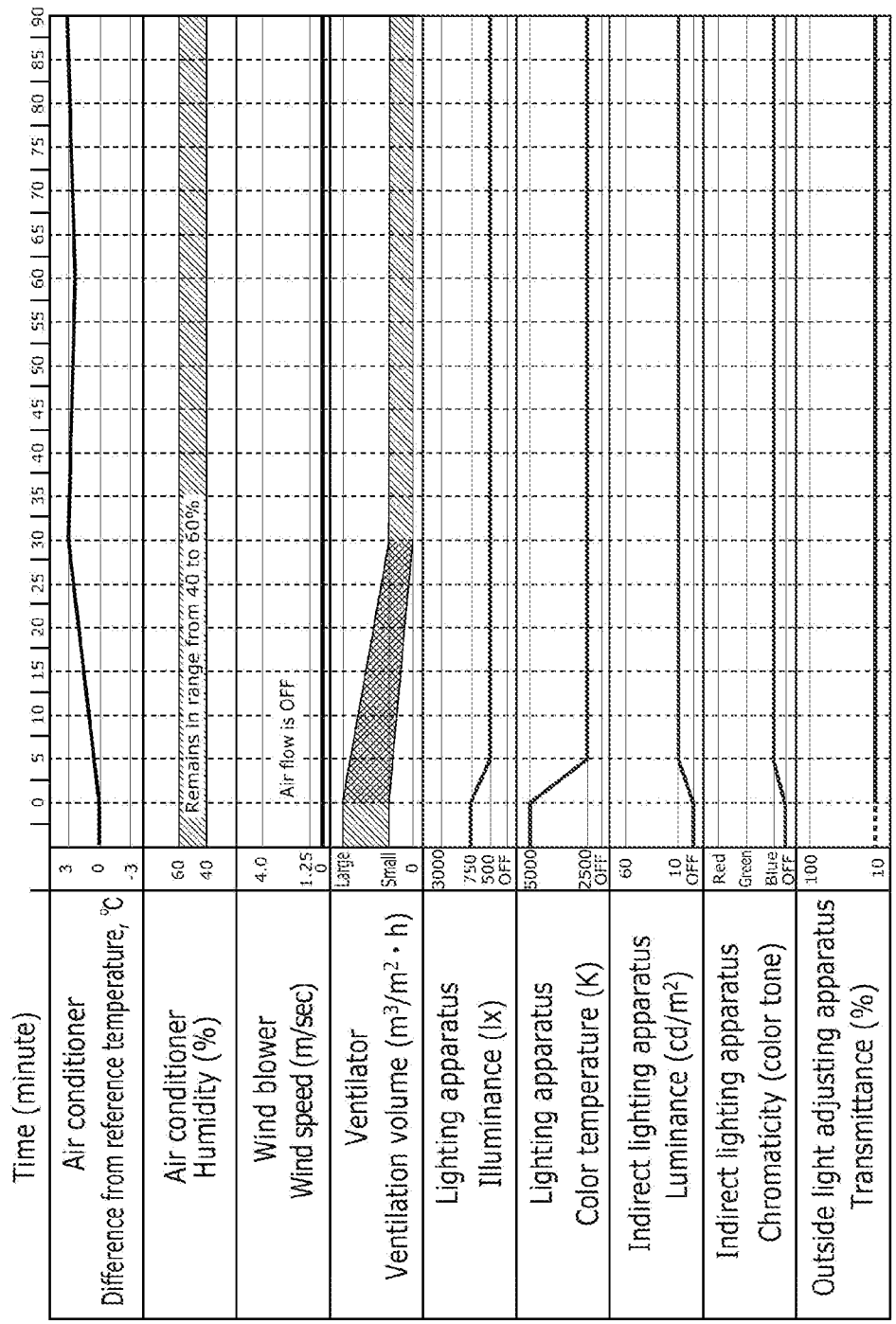
FIG. 5 is a time chart for explaining second control which makes a function of a parasympathetic nervous system of the subject dominant.

As described above, environmental control system 10 is capable of performing the second control making the function of the parasympathetic nervous system of subject 200 dominant. Hereinafter, details of the second control are described. FIG. 5 is a time chart for explaining the control making the function of the parasympathetic nervous system of subject 200 dominant. It is assumed that, in FIG. 5, the start time of the second control is 0 minute, and as one example, target apparatuses are being controlled with consideration of only comfortableness before the start time. Although a period from 0 minute to 90 minutes is illustrated in FIG. 5, the same control as performed in the period from 0 minute to 90 minutes is repeated after the period.

It is to be noted that, in the second control making the function of the parasympathetic nervous system dominant, it is only necessary that at least one of the target apparatuses be controlled, but two or more of the target apparatuses may be controlled. This can make the function of the parasympathetic nervous system of subject 200 to further dominant.

First, control on air conditioner 30 is described. Controller 121 of control apparatus 120 increases a temperature in space 300 using air conditioner 30 in an initial period from the start of the second control making the function of the parasympathetic nervous system dominant. Specifically, controller 121 increases the surrounding temperature from a reference temperature by 3 degrees Celsius for 30 minutes immediately after the start of the control. It is to be noted that the time (30 minutes) required to increase the temperature is one example, and is not particularly limited. It is desirable that the surrounding temperature be increased by approximately 3 degrees Celsius for 30 minutes.

Providing an environment in which a temperature in space 300 is slightly warmer than a reference temperature makes the function of the parasympathetic nervous system of subject 200 dominant. Reference temperatures differ depending on seasons. For example, reference temperatures are a predetermined temperature in a range from 25 degrees Celsius to 27 degrees Celsius in summer, a predetermined temperature in a range from 21 degrees Celsius to 23 degrees Celsius in spring and autumn, and a predetermined temperature in a range from 17 degrees Celsius to 20 degrees Celsius in winter.

Controller 121 subsequently decreases the surrounding temperature by 1 degree Celsius for 30 minutes, and then increases the surrounding temperature by 1 degree Celsius for 30 minutes. After the above changes, such temperature changes are repeated. In other words, controller 121 cyclically changes the temperature in space 300 using air conditioner 30 in such a manner that the temperature difference from a largest value to a smallest value falls within 3 degrees Celsius. Surrounding temperatures around subject 200 are measured by, for example, environment measuring apparatus 100. Controller 121 controls air conditioner based on the temperatures measured by environment measuring apparatus 100. Controller 121 may increase and decrease a temperature to be set of air conditioner 30 at the 60-minute cycle as described above without using environment measuring apparatus 100. It is to be noted that the cycle (60-minute cycle) for changing the temperatures is one example, and is not limited particularly.

In this way, controller 121 increases and decreases the temperature slightly (specifically, by approximately 3 degrees Celsius or less) at the predetermined cycle (for example, at the 60-minute cycle). In general, a human repeats basal metabolism in which his/her body is cooled down by sweating when the body generates heat excessively, and his/her body generates heat again after an elapse of time. Keeping a surrounding temperature around subject 200 constant leads to ignoring such a basal metabolism, and thus subject 200 inevitably feels too hot or too cold.

In comparison, slightly changing temperatures at a cycle with consideration of the body metabolism of subject 200 can increase comfortableness while reducing stimuli by temperatures given to subject 200. This can make the function of the parasympathetic nervous system of subject 200 dominant.

Controller 121 keeps a humidity in space 300 in a range from 40% to 60% using air conditioner 30 which the second control making the function of the parasympathetic nervous system dominant.

[Second Control: Control on the Ventilator]

Next, control on ventilator 70 is described. Controller 121 sets the concentration of carbon dioxide in space 300 to 1000 ppm or more using ventilator 70. For example, controller 121 sets the concentration of carbon dioxide in space 300 to 1000 ppm or more by decreasing the ventilation volume of ventilator 70 when the concentration of the carbon dioxide in space 300 is low. 1000 ppm is one example of a predetermined concentration. Controller 121 may set the concentration of the carbon dioxide in space 300 to 1000 ppm or more by stopping ventilator 70. For example, the concentration of the carbon dioxide in space 300 is measured by environment measuring apparatus 100, and controller 121 controls ventilator 70 based on the concentration of the carbon dioxide measured by environment measuring apparatus 100.

Adjusting the concentration of the carbon dioxide in space 300 to 1000 ppm or more in this way can make the function of the parasympathetic nervous system of subject 200 dominant.

[Second Control: Control on the Other Apparatuses]

Hereinafter, control on the other target apparatuses is described while further referring to FIG. 5.

First, control on wind blower 20 is described. Controller 121 stops the wind blown by wind blower 20 in the second control making the function of the parasympathetic nervous system dominant. Although wind blower 20 is stopped before the start of the control in the example in FIG. 5, control of stopping wind blower 20 is performed if wind blower 20 is operating before the start of control.

Since this reduces stimuli given to subject 200 by the wind blown by wind blower 20, it becomes possible to make the function of the parasympathetic nervous system dominant. It is to be noted that control for decreasing a wind speed more than the wind speed before the start of the control may be performed when wind blower 20 is operating before the start of the control. Even such control can make the function of the parasympathetic nervous system dominant.

Next, control on lighting apparatus 40 is described. Controller 121 decreases an illuminance in space 300 using lighting apparatus 40 in the initial period from the start of the second control making the function of the parasympathetic nervous system dominant. For example, controller 121 decreases the illuminance that is initially 750 lx in space 300 down to 500 lx for 5 minutes from the start of the control. It is desirable that the illuminance be changed with time in such a manner that subject 200 does not feel uncomfortable due to illuminance changes. "Decreasing the illuminance of lighting apparatus 40 in space 300" includes turning off lighting apparatus 40.

Reducing the illuminance in space 30 in this way reduces the stimuli by light given to subject 200, which can make the function of the parasympathetic nervous system of subject 200 dominant.

In addition, controller 121 decreases the color temperature of the light emitted by lighting apparatus 40 in the initial period from the start of the second control making the function of the parasympathetic nervous system dominant. It is desirable that the chromaticity be changed with time in such a manner that subject 200 does not feel uncomfortable due to chromaticity changes. In the example in FIG. 5, the color temperature that was 5000 K initially of light emitted by lighting apparatus 40 is decreased to 2500 K.

In this way, providing space 300 with an illuminance environment in which the color temperature is low can make the function of the parasympathetic nervous system of subject 200 dominant.

Next, control on outside light adjusting apparatus 50 is described. Controller 121 decreases a light amount of outside light that enters space 300 using outside light adjusting apparatus 50 in the initial period from the start of the second control making the function of the parasympathetic nervous system dominant. Specifically, controller 121 decreases a light transmittance of outside light adjusting apparatus 50. It is desirable that the illuminance be changed with time in such a manner that subject 200 does not feel uncomfortable due to illuminance changes. "Decreasing light transmittance of outside light adjusting apparatus 50" includes setting a transmittance rate of outside light adjusting apparatus 50 to 0% to block light.

Reducing the illuminance in space 30 in this way reduces the stimuli by light given to subject 200, which can make the function of the parasympathetic nervous system of subject 200 dominant.

Next, control on indirect lighting apparatus 60 is described. Controller 121 changes an emission color of light to be emitted by indirect lighting apparatus 60 in the second control making the function of the parasympathetic nervous system dominant. For example, controller 121 increases a luminance (substantially, an illuminance) from 0 (colorless) $cd/m^2$ to 10 $cd/m^2$ for 5 minutes from the start of the control. The emission color at this time is blue for example, but may be emerald green, or another color. It is only necessary that controller 121 changes the chromaticity of the light to be emitted by indirect lighting apparatus 60 in such a manner that the x-coordinate in a chromaticity diagram of a CIE 1931 color space of the chromaticity decreases in the initial period from the start of the second control making the function of the parasympathetic nervous system dominant. This can make the function of the parasympathetic nervous system of subject 200 dominant.

Alternatively, controller 121 may cause indirect lighting apparatus 60 to emit light having a favorite emission color of subject 200 in the second control making the function of the parasympathetic nervous system dominant. The Inventors have found out that it is possible to make the function of the parasympathetic nervous system dominant effectively more than a case in which other apparatuses such as wind blower 20 are controlled, by causing indirect lighting apparatus 60 to emit light having the favorite emission color of subject 200. Such control of causing indirect lighting apparatus 60 to emit light having a favorite emission color of subject 200 is described in detail later in the section of [Other Control Using the Indirect Lighting Apparatus].

Controller 121 fluctuates the illuminance of the light to be emitted by indirect lighting apparatus 60 although the control is not precisely illustrated in FIG. 5. In other words, the brightness of the light to be emitted by indirect lighting apparatus 60 is increased or decreased at one or more cycles of several seconds that are in a range approximately from 1 second to 10 seconds (a constant cycle or random cycles are possible). The light to be emitted by indirect lighting apparatus 60 may fluctuate with constant amplification or with random amplification. For example, controller 121 may fluctuate the illuminance of the light to be emitted by indirect lighting apparatus 60 as indicated by a wind speed waveform in FIG. 4. This can make the function of the parasympathetic nervous system of subject 200 dominant.

Next, control on speaker 80 and scent generator 90 is described. Controller 121 changes a sound to be output by speaker 80 in the second control making the function of the parasympathetic nervous system dominant. "Changing a sound" here includes starting to output a sound in a state in which no sound is output. For example, speaker 80 outputs a sound which provides a relaxing effect such as a healing musical piece or a comparatively slow-tempo musical piece. This can make the function of the parasympathetic nervous system of subject 200 dominant.

Controller 121 changes a scent to be generated by the scent generator in the second control making the function of the parasympathetic nervous system dominant. "Changing a scent" here includes starting to generate a scent in a state in which no scent is generated. Scent generator 90 generates a low-stimulus scent in which phytoncide, etc. is included, a scent of lavender, or the like. This can make the function of the parasympathetic nervous system of subject 200 dominant.

[Other Control Using the Indirect Lighting Apparatus: Outline]

Figure 6:
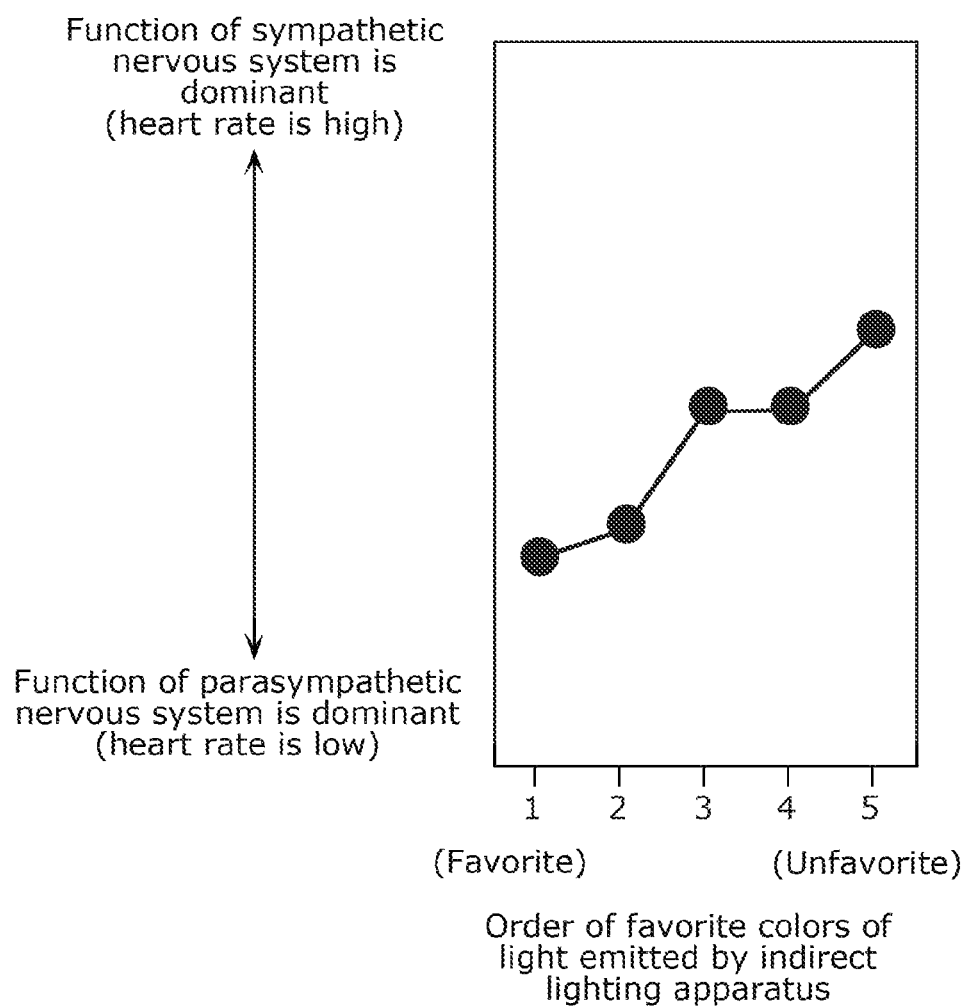
FIG. 6 is a diagram indicating an analysis result of an experiment performed by the Inventors.

Hereinafter, other control on indirect lighting apparatus 60 is described. The Inventors have found out that it is possible to adjust the function of the sympathetic nervous system and the function of the parasympathetic nervous system by causing indirect lighting apparatus 60 to emit light having a favorite emission color of subject 200 and to emit light having an unfavorite emission color of subject 200. FIG. 6 is a diagram indicating an analysis result of an experiment performed by the Inventors.

In the experiment, first, subject 200 provides five emission colors of light with favorite-unfavorite ranks while watching indirect lighting apparatus 60 which is actually emitting light of five colors that are red, yellow, white, green, and blue.

Next, subject 200 is kept staying in space 300 having an environment controlled based on a plurality of environment parameters including emission colors of light that are emitted by indirect lighting apparatus 60, and the heart rates of subject 200 are measured. As indicated in FIG. 12 to be described later, the heart rates can be used as indicators indicating the function of the sympathetic nervous system. The function of the sympathetic nervous system is more dominant as the heart rate is higher, and the function of the parasympathetic nervous system is more dominant as the heart rate is lower.

It is to be noted that examples of the plurality environment parameters include the wind speed of wind to be blown, a temperature, the concentration of carbon dioxide, the illuminance of light to be emitted by lighting apparatus 40, the color temperature of light to be emitted by lighting apparatus 40, a scent, a sound, other than emission colors of light that are emitted by indirect lighting apparatus 60. In the experiment, subject 200 is kept staying and the heart rate of subject 200 is measured in each of approximately twenty environments each having a different combination of the plurality of environment parameters.

As illustrated in FIG. 6, statistical analysis of the result of the experiment shows that the order of the subject's favorites of emission colors of light emitted by indirect lighting apparatus 60 among the plurality of parameters have a strong correlation with the function of the autonomic nervous system. Specifically, the analysis shows that causing indirect lighting apparatus 60 to emit light having a subject's favorite color makes the function of the parasympathetic nervous system dominant (in other words, the heart rate decreases), and that causing indirect lighting apparatus 60 to emit light having a subject's unfavorite color makes the function of the sympathetic nervous system dominant (in other words, the heart rate increases). It is to be noted that the contribution of the favorite-unfavorite in emission color of light emitted by indirect lighting apparatus 60 is 33.96%, and is comparatively high in the contribution of the plurality of environment parameters used in the experiment. A P value indicating a significance is 0.042. It can be said that the favorite-unfavorite in emission color of light emitted by indirect lighting apparatus 60 significantly affects the function of the autonomic nervous system (specifically, the heart rates).

Based on the analysis result, controller 121 may cause indirect lighting apparatus 60 to emit light having an unfavorite color of subject 200 in the first control and cause indirect lighting apparatus 60 to emit light having a favorite color of subject 200 in the second control.

[Other Control Using the Indirect Lighting Apparatus: Settings]

Figure 7:
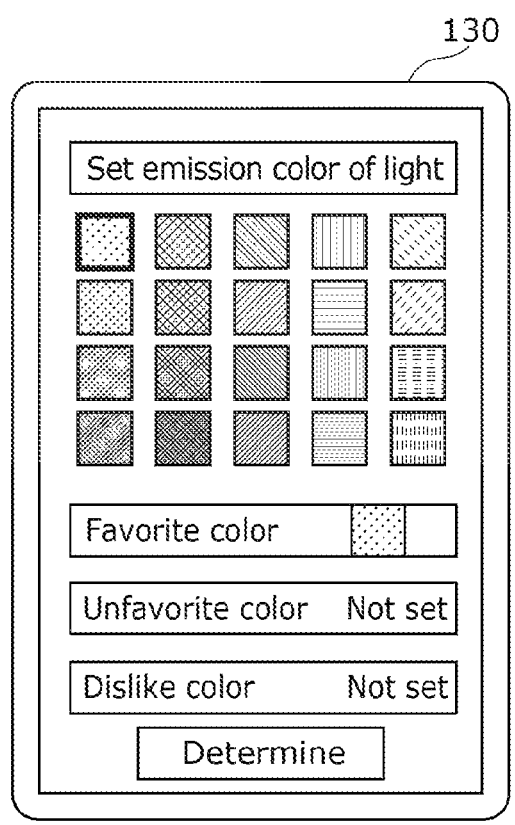
FIG. 7 is a diagram illustrating one example of a screen for setting an emission color of light displayed on a setting apparatus.

Setting apparatus 130 receives, in advance, settings of an unfavorite emission color of light that subject 200 likes and a favorite emission color of light that subject 200 does not like, from subject 200. FIG. 7 is a diagram illustrating one example of a screen for setting an emission color of light displayed on setting apparatus 130.

A plurality of candidate emission colors are displayed on the screen for setting. Subject 200 is able to set the favorite emission color and the unfavorite emission color among the candidates. It is to be noted that subject 200 is able to set a dislike emission color optionally in the example in FIG. 7. The emission color which has been set as the dislike emission color is excluded from emission colors of light to be emitted by indirect lighting apparatus 60.

It is only necessary that at least one favorite emission color be set in the setting of emission colors. If favorite emission color is set, the other emission colors can be handled as unfavorite emission colors. In the setting of the emission colors, a plurality of favorite emission colors and a plurality of unfavorite emission colors may be set. Furthermore, a favorite emission color and an unfavorite emission color may be set for each unit such as a time period, a weekday/holiday, a season.

Figure 8:
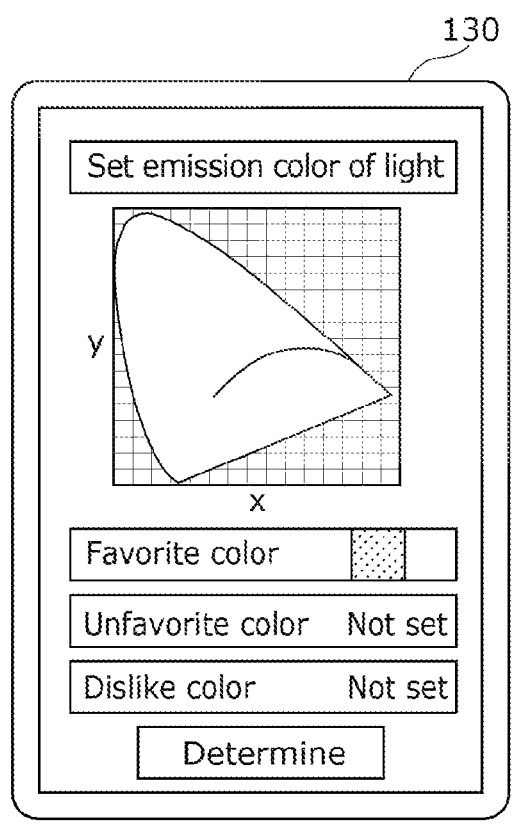
FIG. 8 is a diagram illustrating another example of a screen for setting an emission color of light displayed on the setting apparatus.

It is to be noted that the screen for setting in FIG. 7 is one example. In the screen for setting, candidate emission colors may be displayed as a color palette. Alternatively, a chromaticity diagram of a CIE 1931 color space may be set on the screen for setting, or an emission color may be set by means of subject 200 specifying the coordinates on the color space. FIG. 8 is a diagram illustrating another example of a screen for setting such an emission color. In the setting of an emission color, not only a hue but also at least one of a luminance and a chrominance may be set.

In general, the rate of green (plants) in a field of view of a human is referred to as a green coverage rate. It is known that a 10% or more green coverage rate reduces a human stress. If an illumination area of light that is emitted by indirect lighting apparatus 60 is 10% or more of a visible area of subject 200, it is possible to adjust the function of the autonomic nervous system more effectively.

Figure 9:
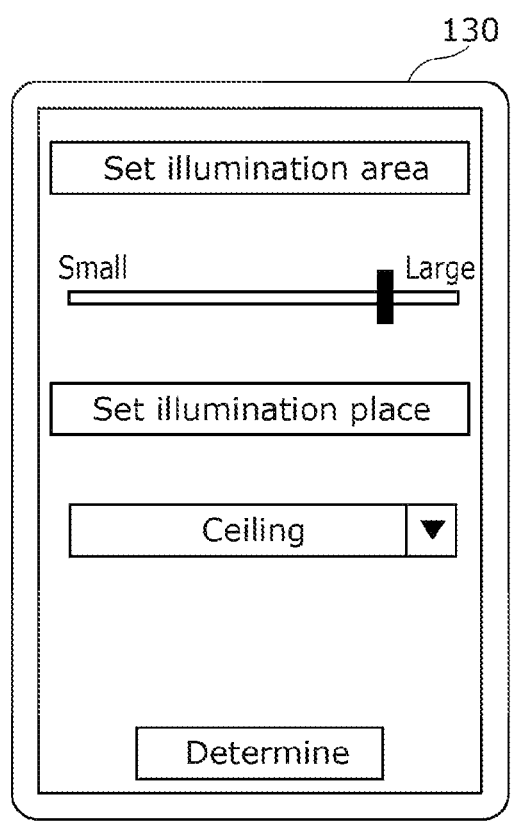
FIG. 9 is a diagram illustrating one example of a screen for setting an illumination area and an illumination place displayed on the setting apparatus.

The illumination area of light that is emitted by indirect lighting apparatus 60 may be set by subject 200 via setting apparatus 130. In this case, setting apparatus 130 receives a setting of an illumination area of light that is emitted by indirect lighting apparatus 60, and control apparatus 120 controls an illumination area of light that is emitted by indirect lighting apparatus 60 to be the illumination area received by setting apparatus 130 in each of the first control and the second control. FIG. 9 is a diagram illustrating one example of a screen for setting an illumination area and an illumination place displayed on a screen for setting.

As illustrated in FIG. 9, for example, subject 200 is able to set an illumination area by performing an operation of drugging a slide bar. It is to be noted that, for example, controller 121 is capable of changing the number of light sources which are caused to emit light among the plurality of light sources of indirect lighting apparatus 60, or changing an illumination area by changing the brightness of light that is emitted by some of the light sources of indirect lighting apparatus 60. When environment control system includes a plurality of indirect lighting apparatuses 60, controller 121 is capable of changing an illumination area by changing the number of indirect lighting apparatuses 60 which are caused to emit light out of the plurality of indirect lighting apparatuses 60.

Furthermore, subject 200 is able to set an illumination place of light that is emitted by indirect lighting apparatus 60 via the screen for setting in FIG. 9. For example, subject 200 is able to make a setting on whether indirect lighting apparatus 60 illuminates a ceiling, a wall, or a floor. At this time, indirect lighting apparatus 60 is configured to be capable of changing an emission direction of light.

It is more user-friendly if a user be able to make settings of an emission color of light, an illumination range, and an illumination place while the user is actually watching how indirect lighting apparatus 60 emits light. In view of this, while setting apparatus 130 is receiving a selection of an emission color for setting the emission color (in other words, while the emission color is being provisionally selected before the setting of the emission color is determined), control apparatus 120 may cause indirect lighting apparatus 60 to emit light having the emission color that is being selected. In other words, a provisional setting state before the setting is determined may be reflected on indirect lighting apparatus 60 in real time. Provisional setting states of an illumination area and an illumination place before settings are determined may also be reflected on indirect lighting apparatus 60 in real time. Being reflected in real time here means that operations on setting apparatus 130 and emission manners by indirect lighting apparatus 60 are substantially synchronized.

[Other Control Using the Indirect Lighting Apparatus: Variations]

Light that is emitted by indirect lighting apparatus 60 may form a pattern on an illumination object (a wall, a ceiling, a floor, or the like) by. Examples of the pattern here include a stripe pattern, a dot pattern, a plant leaf pattern, and a pattern of clouds in the sky. These patterns may change with time. In this case, an optical system capable of projecting a pattern in the same manner as a projector is applied as indirect lighting apparatus 60. The pattern to be formed is set, for example, via setting apparatus 130 by subject 200.

Changing an emission color of light that is emitted by indirect lighting apparatus 60 is substantially the same as changing the color of a wall, or the like in space 300 in which subject 200 is located. In view of this, when a wall paper is implemented by a thin display, or the like, and the color or pattern of the wall paper itself can be changed, controller 121 may control the wall paper instead of indirect lighting apparatus 60. The same advantageous effects can be obtained when the wall paper is controlled as in the case where indirect lighting apparatus 60 is controlled. However, in order to easily change the color of a wall, the ceiling, or the like having a large area, it is desirable that an indirect lighting apparatus be used.

Controller 121 may fluctuate the illuminance of light that is emitted by indirect lighting apparatus 60 also in each of cases of causing indirect lighting apparatus 60 to emit light having a favorite emission color of subject 200 or light having an unfavorite emission color of subject 200. As described above, manners of fluctuating illuminance of light are not particularly limited.

Operation Example 1

Figure 10:
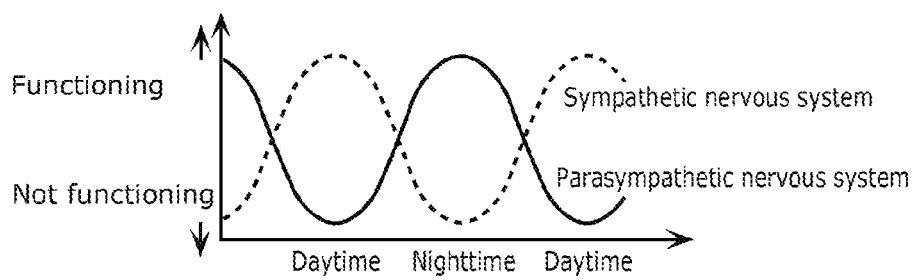
FIG. 10 is a diagram illustrating the function of the sympathetic nervous system and the function of the parasympathetic nervous system.

In general, in the human autonomic nervous system, the function of the sympathetic nervous system is dominant over the function of the parasympathetic nervous system in daytime, and the function of the parasympathetic nervous system is dominant over the function of the sympathetic nervous system in nighttime. FIG. 10 is a diagram illustrating the function of the sympathetic nervous system and the function of the parasympathetic nervous system. In other words, it can be said that a first time period in which the function of the sympathetic nervous system should be made dominant and a second time period in which the function of the parasympathetic nervous system should be made dominant are roughly determined.

Figure 11:
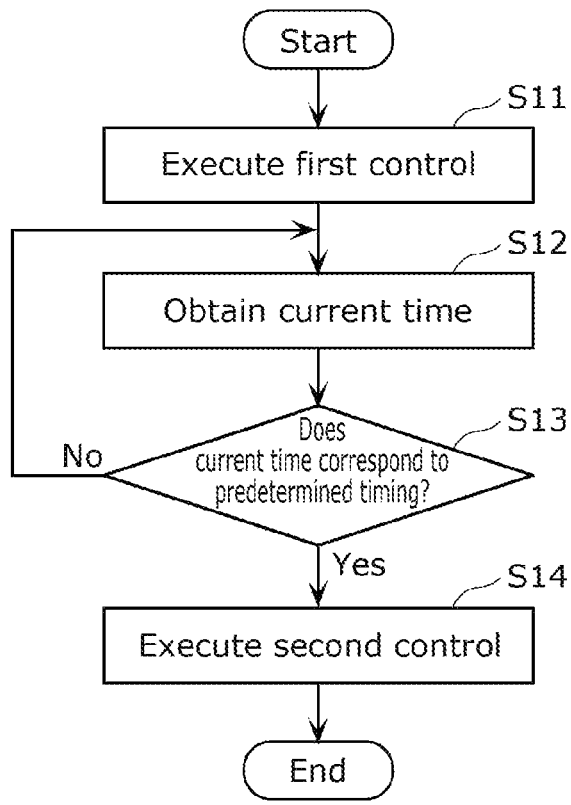
FIG. 11 is a flow chart of operation example 1 of an environmental control system according to an embodiment.

In view of this, control apparatus 120 switches between first control making the sympathetic nervous system dominant and second control making the parasympathetic nervous system dominant at a predetermined timing, based on current time information. FIG. 11 is a flow chart in operation example 1, Operation 1 indicated in FIG. 11 is an example in which the first control that is being executed is switched to the second control, but a second control that is being executed is switched to a first control in the same manner.

In the execution of the first control making the sympathetic nervous system dominant (S11), controller 121 obtains a current time that is measured by time counter 123 (S12), and determines whether the obtained current time corresponds to the predetermined timing (S13). The predetermined timing corresponds to, for example, 8:00 p.m., and is preset, but may be set through a setting operation by subject 200 received by setting apparatus 130.

When determining that the current time corresponds to the predetermined timing (Yes in S13), controller 121 executes the second control making the function of the parasympathetic nervous system dominant (S14). When determining that the current time does not correspond to the predetermined timing (No in S13), controller 121 keeps obtaining a current time (S12) and determining whether the current time corresponds to the predetermined timing (S13).

In this way, environmental control system 10 obtains the current time information, and switches between the first control and the second control at the predetermined timing based on the obtained current time information. In this way, environmental control system 10 is capable of executing the first control and the second control at time periods in which the first control and the second control should be executed respectively. In other words, it is possible to reduce the disorder of the autonomic nervous system of subject 200.

Operation Example 2

Control apparatus 120 may obtain biological information of subject 200, and switch between the first control and the second control at a predetermined timing based on the obtained biological information. The biological information is measured by biological information measuring apparatus 110. FIG. 12 is a diagram illustrating a relationship between the function of the sympathetic nervous system and the function of the parasympathetic nervous system, and change in biological information. As indicated in FIG. 12, the biological information of subject 200 relates to the function of the sympathetic nervous system and the function of the parasympathetic nervous system. The biological information includes, for example, measured data of body temperatures, blood pressures, heart rates, pulse waves, the amounts of sweating, pupil diameters, epidermis temperatures, and facial expressions. The measured data of the biological information can be used as indicators for switching between the first control and the second control.

Figure 13:
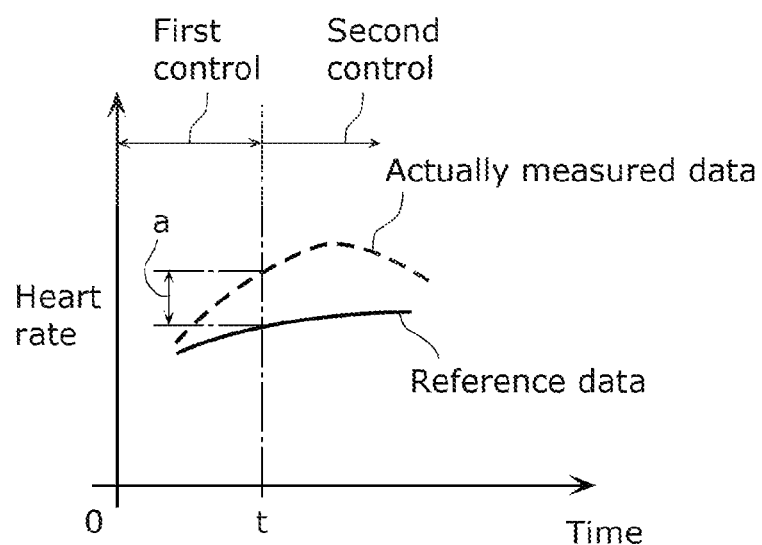
FIG. 13 is a diagram for explaining control based on heart rates.

FIG. 13 is a diagram for explaining switching timings of control based on heart rates. FIG. 13 is a diagram for explaining the timings for switching the first control that is being executed to the second control. For example, changes in heart rate in resting periods in several days of subject 200 are obtained, and the average change in heart rate per day is stored as reference data of the heart rate onto storage 124. The reference data is indicated by a solid line in FIG. 13. Although the reference data is optimized for subject 200, it is to be noted that absolute reference data to be applied to any person can be used instead of the reference data.

Controller 121 monitors the heart rate of subject 200 measured by biological information measuring apparatus 110, and compares the heart rate with reference data stored in storage 124. When the heart rate is lower than the reference data, the function of the sympathetic nervous system is estimated to be weak, and it is considered that the first control making the function of the sympathetic nervous system dominant needs to be performed. In addition, when the heart rate is higher than the reference data, the function of the parasympathetic nervous system is estimated to be weak, and it is considered that the control making the function of the parasympathetic nervous system dominant.

In view of this, as indicated in FIG. 13, for example, controller 121 switches the first control to the second control at time t as a predetermined timing at which the heart rate that is measured by biological information measuring apparatus 110 becomes larger than the reference data by threshold value a (a>0). Although not illustrated, controller 121 may switch the second control to the first control at a time corresponding to the predetermined timing at which the heart rate that is measured by biological information measuring apparatus 110 becomes smaller than the reference data by threshold value a.

When the function of the parasympathetic nervous system of subject 200 is estimated to be weaker than normal, environmental control system 10 is capable of executing the second control making the function of the parasympathetic nervous system dominant. When the function of the sympathetic nervous system of subject 200 is estimated to be weaker than normal, environmental control system 10 is capable of executing the first control making the function of the sympathetic nervous system dominant. In other words, it is possible to reduce the disorder of the autonomic nervous system of subject 200. It is to be noted that the same operation can be performed using biological information other than the heart rates.

Operation Example 3

Figure 14:
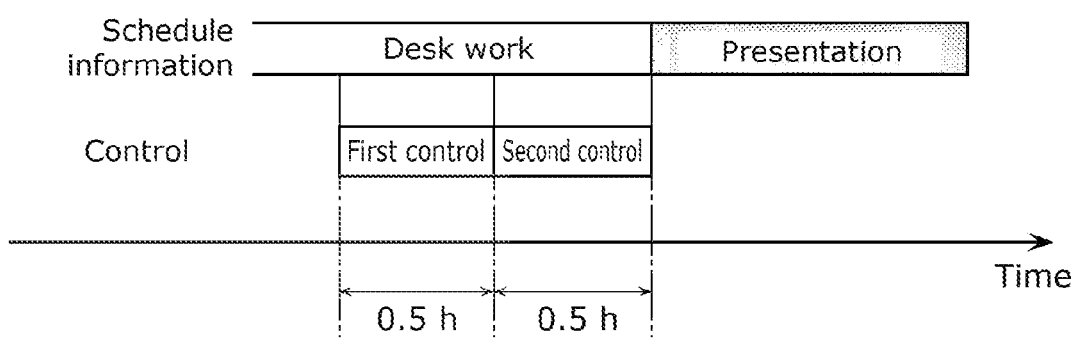
FIG. 14 is a diagram illustrating schedule information of the subject and a control switching timing.

Control apparatus 120 may obtain schedule information of subject 200, and switch between the first control and the second control at a predetermined timing, based on the schedule information. FIG. 14 is a diagram illustrating schedule information of subject 200 and a control switching timing. For example, such schedule information is pre-stored in storage 124 by setting apparatus 130 receiving an operation for inputting a schedule from a user such as subject 200.

As indicated in FIG. 14, it is assumed that a presentation by subject 200 is scheduled in schedule information. When subject 200 is estimated to be nervous before the presentation as indicated, a wakefulness of subject 200 is once increased and then subject 200 is allowed to be relaxed instead of simply being allowed to be relaxed. In this way, subject 200 has an alleviated feeling of nervousness and a feeling of relaxing in good balance during the presentation, which enables subject 200 to exert the high performance.

In view of this, when an hour is left before a next schedule (for example, a presentation), controller 121 executes the first control during initial 30 minutes, and then the second control after the initial 30 minutes. In this way, subject 200 has the feeling of nervousness and the feeling of relaxing in good balance during the presentation, which enables subject 200 to exert the high performance.

It is to be noted that the timing for switching between the first control and the second control can be changed according to, for example, biological information measured by biological information measuring apparatus 110. For example, an operation example is conceived in which the first control is executed until the heart rate of the subject reaches a predetermined value, and then the first control is switched to the second control. It is to be noted that the first control and the second control can be switched suitably for a behavior other than the presentation before the behavior.

[Variations]

Regarding indirect lighting apparatus 60, control apparatus 120 may change the chromaticity of light to be emitted by indirect lighting apparatus 60 in such a manner that at least one of an x coordinate and a y coordinate in a chromaticity diagram of a CIE 1931 color space of the chromaticity is different between the first control and the second control. In other words, control apparatus 120 may change the chromaticity of the light to be emitted by indirect lighting apparatus 60 in the manner that the chromaticity is different between the first control and the second control.

[Effects, Etc.]

As described above, environmental control system 10 includes: indirect lighting apparatus 60 which is disposed in space 300 in which subject 200 is located and is capable of changing an emission color of light; setting apparatus 130 which receives settings of a favorite emission color of light that subject 200 likes and an unfavorite emission color of light that subject 200 does not like; and control apparatus 120 which switches between first control and second control at a predetermined timing, the first control making a function of a sympathetic nervous system of subject 200 dominant over a function of a parasympathetic nervous system of subject 200 by causing indirect lighting apparatus 60 to emit light having the unfavorite emission color of subject 200 received by setting apparatus 130, the second control making the function of the sympathetic nervous system of subject 200 dominant over the function of the parasympathetic nervous system of subject 200 by casing indirect lighting apparatus 60 to emit light having the favorite emission color of subject 200 received by setting apparatus 130.

Environmental control system 10 is capable of switching between the first control and the second control by changing the emission color of light that is emitted by indirect lighting apparatus 60. Environmental control system 10 is capable of reducing the disorder of the autonomic nervous system of subject 200 by switching between the first control and the second control at the predetermined timing. It is to be noted that the present invention may be implemented as an environmental control system which performs at least one of the first control and the second control.

In addition, for example, an illumination area of light that is emitted by indirect lighting apparatus 60 is 10% or more of an area visible to subject 200.

Environmental control system 10 is capable of effectively reducing the disorder of the autonomic nervous system of subject 200.

In addition, for example, when setting apparatus 130 receives selection of the emission color for setting the emission color, control apparatus 120 causes indirect lighting apparatus 60 to emit light having the emission color selected.

Environmental control system 10 allows subject 200 to easily set his/her favorite emission color of light.

In addition, for example, light that is emitted by indirect lighting apparatus 60 forms a pattern on an illumination object.

Environmental control system 10 is capable of causing light that is emitted by indirect lighting apparatus 60 to form a pattern on an illumination object.

Furthermore, for example, control apparatus 120 fluctuates light that is emitted by indirect lighting apparatus 60 in each of the first control and the second control.

Environmental control system 10 is capable of executing the first control and the second control which fluctuate the light that is emitted by indirect lighting apparatus 60.

In addition, for example, environmental control system 10 further includes environment measuring apparatus 100 which measures environmental information in space 300 in which subject 200 is located. Control apparatus 120 switches between the first control and the second control at the predetermined timings, based on the environmental information measured. Environment measuring apparatus 100 is one example of a measuring apparatus.

Environmental control system 10 is capable of executing each of the first control and the second control, based on the environmental information in space 300.

In addition, for example, control apparatus 120 obtains current time information, and switches between the first control and the second control at the predetermined timing, based on the current time information obtained.

Environmental control system 10 is capable of executing the first control and the second control at time periods in which the first control and the second control should be performed respectively. In other words, it is possible to reduce the disorder of the autonomic nervous system of subject 200.

In addition, for example, control apparatus 120 obtains biological information of subject 200, and switches between the first control and the second control at the predetermined timing, based on the obtained biological information of subject 200.

Based on the biological information, environmental control system 10 is capable of executing the first control when the function of the sympathetic nervous system of subject 200 is estimated to be weaker than normal, and executing the second control when the function of the parasympathetic nervous system of subject 200 is estimated to be weaker than normal. In other words, it is possible to reduce the disorder of the autonomic nervous system of subject 200.

In addition, control apparatus 120 obtains schedule information of subject 200, and switches between the first control and the second control at the predetermined timing, based on the obtained schedule information of subject 200.

Environmental control system 10 is capable of allowing subject 200 to exert a high performance by switching between the first control and the second control suitably to a behavior determined in the schedule information.

Furthermore, an environmental control method which is executed by a computer such as environmental control system 10 includes: receiving settings of a favorite emission color of light that subject 200 likes and an unfavorite emission color of light that subject 200 does not like; and switching between first control and second control at a predetermined timing, the first control making a function of a sympathetic nervous system of subject 200 dominant over a function of a parasympathetic nervous system of subject 200 by causing indirect lighting apparatus 60 which is disposed in space 300 in which subject 200 is located and is capable of changing an emission color of light to emit light having the unfavorite emission color of subject 200 received, the second control making the function of the sympathetic nervous system of subject 200 dominant over the function of the parasympathetic nervous system of subject 200 by casing indirect lighting apparatus 60 to emit light having the favorite emission color of subject 200 received.

The environmental control method makes it possible to switch between the first control and the second control by changing the emission color of light that is emitted by indirect lighting apparatus 60. The environmental control method makes it possible to reduce the disorder of the autonomic nervous system of subject 200 by switching between the first control and the second control at the predetermined timing.

As described above, for example, environmental control system 10 includes: wind blower 20 which blows wind toward subject 200; and control apparatus 120 which switches between first control and second control at a predetermined timing, the first control making a function of a sympathetic nervous system of subject 200 dominant over a function of a parasympathetic nervous system of subject 200 by changing a wind speed of the wind that is blown by wind blower 20 at a predetermined cycle, and the second control making the function of the parasympathetic nervous system of subject 200 dominant over the function of the sympathetic nervous system of subject 200 by decreasing a wind speed of the wind that is blown by wind blower 20 to a wind speed lower than the wind speed in the first control.

Environmental control system 10 is capable of switching between the first control and the second control by changing details of control on wind blower 20. Environmental control system 10 is capable of reducing the disorder of the autonomic nervous system of subject 200 by switching between the first control and the second control at the predetermined timing.

In addition, for example, the predetermined cycle is a cycle in a range from 15 minutes to 60 minutes, and a time during which a wind speed is a smallest value in the first control is less than or equal to 50% of the predetermined cycle.

Environmental control system 10 is capable of constantly giving stimuli by wind to subject 200 by changing the wind speed with time in the first control. This prevents subject 200 from getting used to the stimuli by wind, which makes it easier to maintain the state in which the function of the sympathetic nervous system is dominant.

In addition, for example, in the first control, control apparatus 120 fluctuates the wind speed of the wind that is blown by wind blower 20 at a time interval shorter than the predetermined cycle.

Environmental control system 10 is capable of constantly giving stimuli by wind to subject 200 by changing the wind speed with time. This prevents subject 200 from getting used to the stimuli by wind, which makes it easier to maintain the state in which the function of the sympathetic nervous system is dominant.

In addition, for example, environmental control system 10 further includes air conditioner 30 for adjusting a temperature in a space in which subject 200 is located. Control apparatus 120 cyclically changes the temperature in space 300 using air conditioner 30 in the first control in such a manner that a temperature difference from a largest value to a smallest value is greater than or equal to a predetermined value (for example, 3 degrees Celsius). Control apparatus 120 cyclically changes the temperature in space 300 using air conditioner 30 in the second control in such a manner that a temperature difference from a largest value to a smallest value falls below the predetermined value (for example, 1 degree Celsius). The predetermined value is, for example, a value larger than 1 degree Celsius and smaller than 3 degrees Celsius.

Environmental control system 10 is capable of switching between the first control and the second control by changing details of the control on air conditioner 30.

In addition, control apparatus 120 decreases a temperature in space 300 using air conditioner 30 in an initial period from a start of the first control; and increases a temperature in space 300 using air conditioner 30 in an initial period from a start of the second control.

Environmental control system 10 is capable of switching between the first control and the second control by changing the details of the control on air conditioner 30 in the initial period from the start of the control on air conditioner 30.

In addition, environmental control system 10 further includes lighting apparatus 40 which illuminates space 300 in which subject 200 is located. Control apparatus 120 increases an illuminance in space 300 using lighting apparatus 40 in an initial period from a start of the first control, and decreases an illuminance in space 300 using lighting apparatus 40 in an initial period from a start of the second control.

Environmental control system 10 is capable of switching between the first control and the second control by changing the details of illuminance control on lighting apparatus 40.

In addition, environmental control system 10 further includes lighting apparatus 40 which illuminates space 300 in which subject 200 is located. Control apparatus 120 increases a color temperature of light emitted by lighting apparatus 40 in an initial period from a start of the first control, and decreases a color temperature of light emitted by lighting apparatus 40 in the initial period from a start of the first control.

Environmental control system 10 is capable of switching between the first control and the second control by changing details of color temperature control on lighting apparatus 40.

In addition, for example, environmental control system 10 further includes indirect lighting apparatus 60 disposed in space 300 in which subject 200 is located. Control apparatus 120 changes a chromaticity of light emitted by the indirect lighting apparatus in such a manner that at least one of an x coordinate and a y coordinate in a chromaticity diagram of a CIE 1931 color space of the chromaticity is different between the first control and the second control.

Environmental control system 10 is capable of performing the first control and the second control by changing details of chromaticity control on indirect lighting apparatus 60.

In addition, environmental control system 10 further includes ventilator 70 which ventilates space 300 in which subject 200 is located. Control apparatus 120 sets a concentration of carbon dioxide in space 300 to a concentration lower than a predetermined concentration using ventilator 70 in the first control, and sets a concentration of carbon dioxide in space 300 to a concentration higher than or equal to the predetermined concentration using ventilator 70 in the second control. The predetermined concentration is 1000 ppm for example.

Environmental control system 10 is capable of switching between the first control and the second control by changing details of control on ventilator 70.

In addition, environmental control system 10 further includes speaker 80 and scent generator 90 which are disposed in space 300 in which subject 200 is located. For example, control apparatus 120 causes speaker 80 to output sounds different between the first control and the second control, and causes scent generator 90 to generate scents different between the first control and the second control. For example, control apparatus 120 causes speaker 80 to output an up-tempo musical piece in the first control, and causes speaker 80 to output a sound which provides a relaxing effect such as a healing musical piece or a slow-tempo musical piece in the second control. In addition, for example, control apparatus 120 causes scent generator 90 to generate a scent of mint in the first control, and causes scent generator 90 to generate a low-stimulus scent in which phytoncide, etc. is included, a scent of lavender, or the like.

Environmental control system 10 is capable of performing the first control and the second control by changing details of control on speaker 80 and scent generator 90.

In addition, for example, an environmental control method which is executed by a computer such as environmental control system 10 includes: switching between first control and second control at a predetermined timing, the first control making a function of a sympathetic nervous system of subject 200 dominant over a function of a parasympathetic nervous system of subject 200 by changing a wind speed of the wind that is blown by wind blower 20 at a predetermined cycle, and the second control making the function of the parasympathetic nervous system of subject 200 dominant over the function of the sympathetic nervous system of subject 200 by decreasing a wind speed of the wind that is blown by wind blower 20 to a wind speed lower than the wind speed in the first control.

Such an environmental control method makes it possible to switch between the first control and the second control by changing details of control on wind blower 20. The environmental control method is capable of reducing the disorder of the autonomic nervous system of subject 200 by switching between the first control and the second control at the predetermined timing.

Other Embodiments

Although the embodiment has been described above, the present invention is not limited to the above embodiment.

For example, in the above embodiment, the processing executed by a particular processing unit may be executed by another processing unit. The order of a plurality of processes may be changed, or a plurality of processes may be executed in parallel.

In the above embodiment, each of the constituent elements may be implemented by a software program suitable for the constituent element being executed. Each of the constituent elements may be implemented by means of a program executer such as a CPU or a processor reading and executing a software program recorded on a recording medium such as hard disc or semiconductor memory.

In addition, each of the constituent elements may be executed by hardware. Each of the constituent elements may be a circuit (or an integrated circuit). These circuits may be configured as a single circuit as a whole, or may be configured as individual circuits. In addition, these circuits may be general-purpose circuits, or dedicated circuits.

Alternatively, the general or specific embodiment of the present invention may be implemented as a system, an apparatus, a method, an integrated circuit, a computer program, or a recording medium such as a computer-readable CD-ROM. Alternatively, the general or specific embodiment of the present invention may be implemented as a combination of a system, an apparatus, a method, an integrated circuit, a computer program, or a recording medium.

For example, the present invention may be implemented as an environmental control method, a program for causing a computer to execute the environmental control method, or a non-transitory computer-readable recording medium on which such a program is recorded.

Alternatively, the present invention may be implemented as a control apparatus according to the embodiment, or as a program which is executed by a computer in order to cause the computer to function as such a control apparatus. Alternatively, the present invention may be implemented as a computer-readable non-transitory recording medium on which such a program is recorded.

In addition, the environmental control system is implemented as a plurality of apparatuses in the embodiment, but may be implemented as a single apparatus. When the environmental control system is implemented as a plurality of apparatuses, the constituent elements of the environmental control system described in the embodiment may be allocated to a plurality of apparatuses in any way.

Furthermore, the present invention encompasses embodiments obtainable by adding, to any of these embodiments, various kinds of modifications that a person skilled in the art would arrive at and embodiments configurable by combining constituent elements in different embodiments without deviating from the scope of the present disclosure.

REFERENCE SIGNS LIST 10 environmental control system
60 indirect lighting apparatus
100 environment measuring apparatus (measuring apparatus)
120 control apparatus
130 setting apparatus
200 subject
300 space

The invention claimed is:

1. An environmental control system, comprising:
an indirect lighting apparatus which is disposed in a space in which a subject is located and is capable of changing an emission color of light;
a setting apparatus which receives settings of a favorite emission color of light that the subject likes and an unfavorite emission color of light that the subject does not like; and
a control apparatus which switches between first control and second control at a predetermined timing, the first control making a function of a sympathetic nervous system of the subject dominant over a function of a parasympathetic nervous system of the subject by causing the indirect lighting apparatus to emit light having the unfavorite emission color of the subject received by the setting apparatus, the second control making the function of the sympathetic nervous system of the subject dominant over the function of the parasympathetic nervous system of the subject by casing the indirect lighting apparatus to emit light having the favorite emission color of the subject received by the setting apparatus.

2. The environmental control system according to claim 1, wherein an illumination area of light that is emitted by the indirect lighting apparatus is 10% or more of an area visible to the subject.

3. The environmental control system according to claim 1, wherein when the setting apparatus receives selection of the emission color for setting the emission color, the control apparatus causes the indirect lighting apparatus to emit light having the emission color selected.

4. The environmental control system according to claim 1, wherein light that is emitted by the indirect lighting apparatus forms a pattern on an illumination object.

5. The environmental control system according to claim 1, wherein the control apparatus fluctuates light that is emitted by the indirect lighting apparatus in each of the first control and the second control.

6. The environmental control system according to claim 1, further comprising:
a measuring apparatus which measures environmental information in the space in which the subject is located,
wherein the control apparatus switches between the first control and the second control at the predetermined timing, based on the environmental information measured.

7. The environmental control system according to claim 1, wherein the control apparatus obtains current time information, and switches between the first control and the second control at the predetermined timing, based on the current time information obtained.

8. The environmental control system according to claim 1, wherein the control apparatus obtains biological information of the subject, and switches between the first control and the second control at the predetermined timing, based on the biological information obtained.

9. The environmental control system according to claim 1, wherein the control apparatus obtains schedule information of the subject, and switches between the first control and the second control at the predetermined timing, based on the schedule information obtained.

10. An environmental control method, comprising:
receiving settings of a favorite emission color of light that the subject likes and an unfavorite emission color of light that the subject does not like; and
switching between first control and second control at a predetermined timing, the first control making a function of a sympathetic nervous system of the subject dominant over a function of a parasympathetic nervous system of the subject by causing an indirect lighting apparatus which is disposed in a space in which a subject is located and is capable of changing an emission color of light to emit light having the unfavorite emission color of the subject received, the second control making the function of the sympathetic nervous system of the subject dominant over the function of the parasympathetic nervous system of the subject by casing the indirect lighting apparatus to emit light having the favorite emission color of the subject received.

* * * * *